US011878148B2

(12) United States Patent
Marici et al.

(10) Patent No.: US 11,878,148 B2
(45) Date of Patent: Jan. 23, 2024

(54) RETAINING ELEMENT TO PREVENT BREAK LOOSE CONTAMINATION FOR PARTIALLY PRE-FILLED SYRINGES

(71) Applicant: Becton, Dickinson and Company, Franklin Lakes, NJ (US)

(72) Inventors: Paul P. Marici, Piscataway, NJ (US); Xiaoyu Sun, Montville, NJ (US); Jonathan Marek Zalot, Ringwood, NJ (US); Youstina Matta, East Brunswick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 687 days.

(21) Appl. No.: 16/909,328

(22) Filed: Jun. 23, 2020

(65) Prior Publication Data
US 2020/0405965 A1  Dec. 31, 2020

Related U.S. Application Data

(60) Provisional application No. 62/868,193, filed on Jun. 28, 2019.

(51) Int. Cl.
*A61M 5/315* (2006.01)
*A61M 5/31* (2006.01)
*A61L 2/08* (2006.01)
*A61L 2/07* (2006.01)

(52) U.S. Cl.
CPC .......... *A61M 5/31501* (2013.01); *A61L 2/07* (2013.01); *A61L 2/08* (2013.01); *A61M 5/3129* (2013.01); *A61M 5/31513* (2013.01); *A61M 5/31563* (2013.01); *A61L 2202/23* (2013.01); *A61M 2005/3114* (2013.01); *A61M 2005/3117* (2013.01); *A61M 2005/31508* (2013.01); *A61M 2207/10* (2013.01)

(58) Field of Classification Search
CPC ...... A61M 5/31501; A61M 2005/3117; A61M 2005/31508
See application file for complete search history.

(56) References Cited

U.S. PATENT DOCUMENTS

| | | | |
|---|---|---|---|
| 4,367,738 A * | 1/1983 | Legendre | A61M 5/5013 604/218 |
| 5,084,017 A | 1/1992 | Maffetone | |
| 2011/0009829 A1 | 1/2011 | Kosinski et al. | |
| 2019/0143047 A1 * | 5/2019 | Jazayeri | A61M 5/14248 604/222 |

FOREIGN PATENT DOCUMENTS

| CN | 109172952 A | 1/2019 |
|---|---|---|
| DE | 102015000999 A1 | 7/2016 |
| WO | 2016094828 A1 | 6/2016 |

OTHER PUBLICATIONS

PCT International Search Report and Written Opinion in PCT/US2020/039348 dated Oct. 20, 2020, 12 pages.

* cited by examiner

*Primary Examiner* — Bradley J Osinski
(74) *Attorney, Agent, or Firm* — Servilla Whitney LLC

(57) ABSTRACT

Syringe assemblies are provided including a partially pre-filled syringe barrel and a plunger rod that incorporates one or more retention elements on the plunger rod that prevents solution from entering a non-sterile area of the syringe when the plunger rod is pulled back. Methods to manufacture a sterilized partially-filled pre-fill syringe assembly are also disclosed.

22 Claims, 10 Drawing Sheets

RETAINING ELEMENT TO PREVENT BREAK LOOSE CONTAMINATION FOR PARTIALLY PRE-FILLED SYRINGES

CROSS-REFERENCE TO RELATED APPLICATIONS

This application claims priority under 35 U.S.C. § 119(e) to U.S. Provisional Application No. 62/868,193, filed Jun. 28, 2019, the disclosures of which are incorporated herein by reference in their entirety.

TECHNICAL FIELD

The present disclosure relates to syringe assemblies and particularly to, syringe assemblies having a plunger rod with a retaining element that prevents solution from entering a non-sterile area of the syringe when pulled back for partially pre-filled syringes. The present disclosure also relates to methods to manufacture a sterilized partially-filled pre-fill syringe assembly.

BACKGROUND

Certain 10 mL syringes which are currently available may include a retaining ring on both the plunger rod and the barrel to prevent the stopper and fluid from moving backward into a non-sterile area. However, the currently available 10 mL syringes having a retaining ring on both the plunger rod and the barrel are not effective to create a partial-filled syringe having a prefilled volume in the range from more than 0 mL to less than 10 mL, e.g. 3 or 5 mL, due to the distance between the retaining ring on the plunger rod and barrel.

There is also a need for a syringe assembly having a plunger rod with retaining element introduced to prevent solution from entering a non-sterile area of the syringe when the plunger rod is accidently pulled back for partially pre-filled syringes.

SUMMARY

Syringe assemblies including a plunger rod with a retaining element that prevents solution from entering a non-sterile area of the syringe when pulled back for partially pre-filled syringes, and methods to manufacture the syringe assemblies are described.

One aspect of the present disclosure pertains to a syringe assembly including a barrel, an open proximal end and a distal end, a plunger rod body disposed within the barrel, and one or more retention elements disposed on the plunger rod. The barrel can include a side wall having an inside surface defining a chamber for retaining a predetermined amount of pre-filled fluid. The distal end includes a distal wall with a tip extending distally therefrom having a passageway therethrough in fluid communication with said chamber. The plunger rod body is disposed within the barrel. The plunger rod can include a distal end including a stopper having a distal face and a proximal end. The one or more retention elements is disposed on the plunger rod at a length from the distal end of the plunger rod configured to provide increased mechanical interference between the plunger rod and barrel when a force is applied in the proximal direction to prevent the pre-filled fluid from entering a non-sterile area of the syringe assembly.

In one or more embodiments, the one or more retention elements include a plurality of discontinuities disposed on the outside surface of the plunger rod.

In one or more embodiments, the one or more retention elements extend radially outwardly toward the inside surface of the barrel.

In one or more embodiments, the predetermined amount of pre-filled fluid is in a range from 0 mL to 10 mL, preferably 1 mL, 2 mL, 3 mL, 4 mL, 5 mL, 6 mL, 7 mL, 8 mL, 9 ml, and 10 mL. In one or more embodiments, the predetermined amount of pre-filled fluid is 3 mL. In one or more embodiments, the predetermined amount of pre-filled fluid is 5 mL.

In one or more embodiments, the one or more retention elements further include at least one discontinuity disposed on the outside surface of the plunger rod, the discontinuity extending radially outwardly toward the inside surface of the barrel; and at least one retaining ring disposed on the inside surface of the barrel, the retaining ring extending radially inwardly toward the outside surface of the plunger rod. In one or more embodiments, the at least one discontinuity cooperating with the at least one retaining ring to increase an interference between the plunger rod and the barrel to require an increased mechanical force to stop the plunger rod from advancing in a proximal direction.

In one or more embodiments, movement of the plunger rod in a proximal direction creates an interference between a retaining ring disposed on an inside surface of the barrel and the one or more retention elements of the plunger.

In one or more embodiments, a portion of the outside surface of the plunger rod is free of retention elements.

In one or more alternate embodiments, the one or more retention elements include a first component having two side walls being level with a straight wall of a crossbar, a sloped top surface having a grade in a range from 1%-100%, one or more flat portions oriented parallel to a longitudinal axis, and a ledge in the sloped top surface that forms a flat end of oriented perpendicular to the longitudinal axis.

In one or more alternate embodiments, the one or more retention elements further include a second component having a tapered wedge that radially protrudes from the straight wall with respect to a medial edge.

In one or more alternate embodiments, the one or more retention elements further include a second component having an oblong protrusion that tapers from the distal end to the proximal end and extends from a curved wall of the crossbar.

In one or more alternate embodiments, the one or more retention elements further include a second component having a slotted hole in the sidewall of the crossbar positionally aligned behind the retention element along the plunger rod.

In one or alternate embodiments, the pre-filled fluid is a solution containing saline, heparin, citrate, pharmaceutical medicament or other drugs, or a combination thereof.

In one or more alternate embodiments, the pre-filled fluid is a medicament. In one or more alternate embodiments, the pre-filled fluid is a flush solution.

In one or more embodiments, the syringe assembly is terminally sterilized or with a sterility claim on the fluid path.

Another aspect of the present disclosure pertains to a method of manufacture of a sterilized partially-filled pre-fill syringe assembly. A barrel is provided including a side wall having an inside surface defining a chamber having a total volume for retaining a predetermined amount of pre-filled fluid, an open proximal end having a retaining protrusion and a distal end including a distal wall with a tip extending distally therefrom having a passageway therethrough in fluid communication with said chamber. A fill volume is preselected, wherein said fill volume is substantially less than said total volume. A plunger rod of one or more embodiments described in the present disclosure is provided. The plunger rod includes one or more retention elements, as described in the present disclosure, disposed on the plunger rod at a distance from the distal end of the plunger rod, said distance correlated to said fill volume. The plunger rod is inserted into the barrel until said retention elements are in a distal position with respect to the retaining protrusion. The barrel is filled with the predetermined amount of the pre-filled fluid to said fill volume, wherein said fill volume is substantially less than said total volume. The barrel tip is sealed with a sealing component. In one or more embodiments, the sealing element is a tip cap. The pre-fill syringe assembly is sterilized. In one or more embodiment, the pre-filled syringe undergoes a terminal sterilization process via either autoclave or radiation sterilization in the manufacturing plant to produce sterile pathways of the pre-filled liquid.

In one or more embodiments, the total volume is approximately 3.33 times the fill volume. In a specific embodiment, the total volume is approximately 10 ml and the fill volume is 3 ml.

In one or more alternate embodiment, the total volume is approximately 2 times the fill volume. In a specific embodiment, the total volume is approximately 10 ml and the fill volume is 5 ml.

DETAILED DESCRIPTION

Before describing several exemplary embodiments of the present disclosure, it is to be understood that the present disclosure is not limited to the details of construction or process steps set forth in the following description. The invention is capable of other embodiments and of being practiced or being carried out in various ways.

Syringe assemblies of the present disclosure include a plunger rod with one or more retaining elements that prevents solution from entering a non-sterile area of the syringe when the plunger is accidentally pulled back for partially prefilled syringes. Syringe assemblies of the present disclosure include one or more retaining element to prevent break loose contamination for partially pre-filled syringes.

Figure 1:
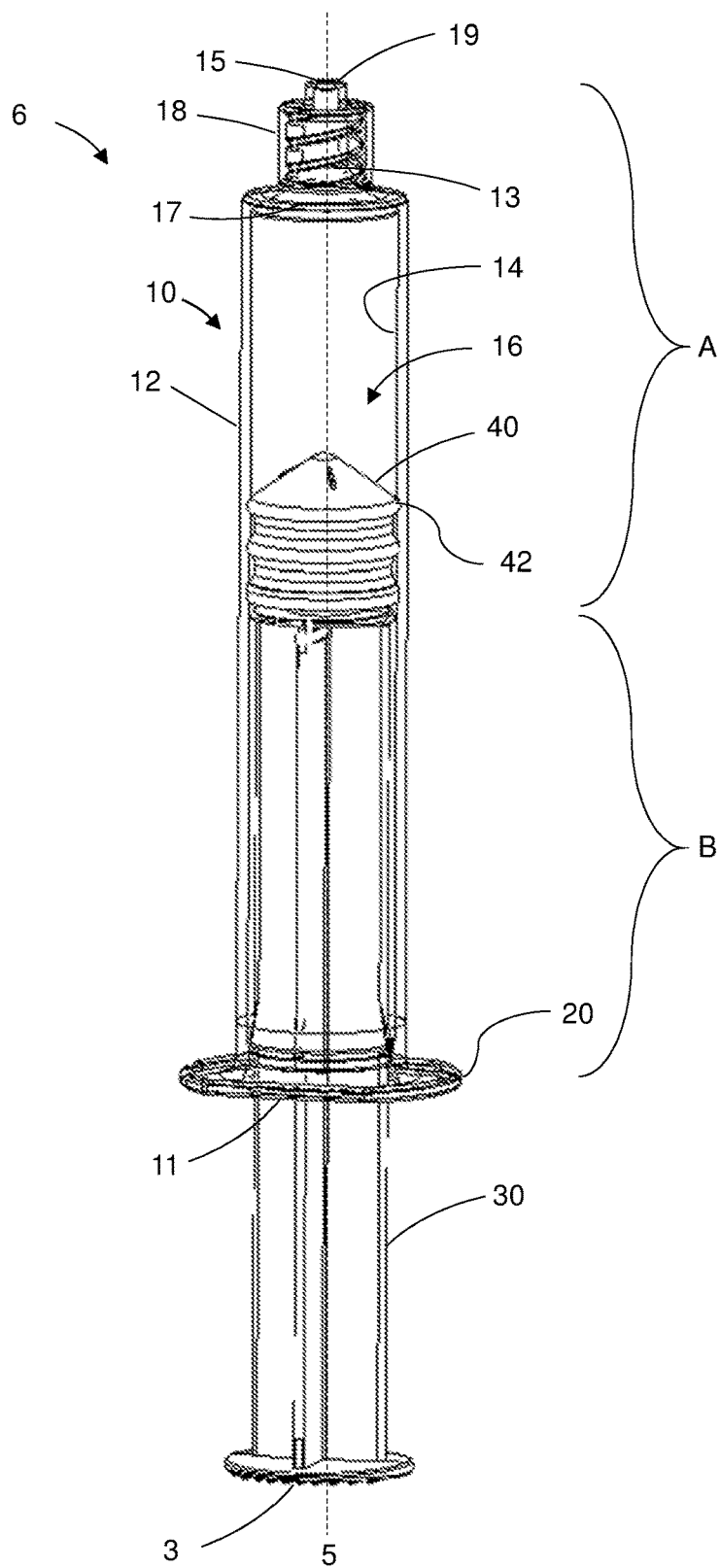
FIG. 1 illustrates a transparent top view of the syringe assembly having a barrel and plunger rod according to one or more embodiments of the present disclosure.

Syringe assemblies according to a first aspect include a syringe barrel and a plunger rod that incorporates a retention element disposed on the plunger rod for interaction with a retaining ring on the syringe barrel. In one or more embodiments, the retaining ring is disposed on an inside surface of the barrel and extends inwardly into the chamber of the barrel. The cross-sectional width of the interior surface of the syringe barrel at the retaining ring is less than the cross-sectional width of the interior surface at the remaining portions of the syringe barrel. In one or more embodiments, the retention feature is in the form of a mechanical stop. One embodiment of the assembled syringe is shown in FIG. 1, with alternative embodiments of a plunger rod to be used with the syringe barrel separately shown in FIGS. 2-9. Referring to FIGS. 1-9, a syringe assembly according to one embodiment comprises a barrel 10 including a side wall 12 having an inside surface 14 defining a chamber 16 for retaining fluid, an open proximal end 11 and a distal end 19 including a distal wall 17 with a tip 15 extending distally therefrom. The tip 15 includes a passageway 13 therethrough in fluid communication with the chamber 16. As shown in FIG. 1, the open proximal end 11 includes finger flanges 20. The side wall 12 of the barrel may be cylindrical or may have another shape.

As shown in FIG. 1, the tip 15 of the barrel may include a locking luer type collar (as shown in FIG. 1) concentrically surrounding tip 15 or a luer slip connection (not shown). In one or more embodiments, the barrel may include a needless connector. In one or more embodiments, the barrel may include conventional medical connectors. The collar 18 may include an inside surface having at least one thread thereon. A needle assembly (not shown) including a cannula having a proximal end, a distal end, and a lumen therethrough may also optionally be provided. A hub (not shown) having an open proximal end containing a cavity and a distal end may be attached to the proximal end of the cannula so that the lumen is in fluid communication with the cavity of the hub. The needle assembly (not shown) is removably attached to the tip of the barrel through engagement of the tip to the cavity of the hub so that the lumen is in fluid communication with the chamber of the barrel.

Figure 3:
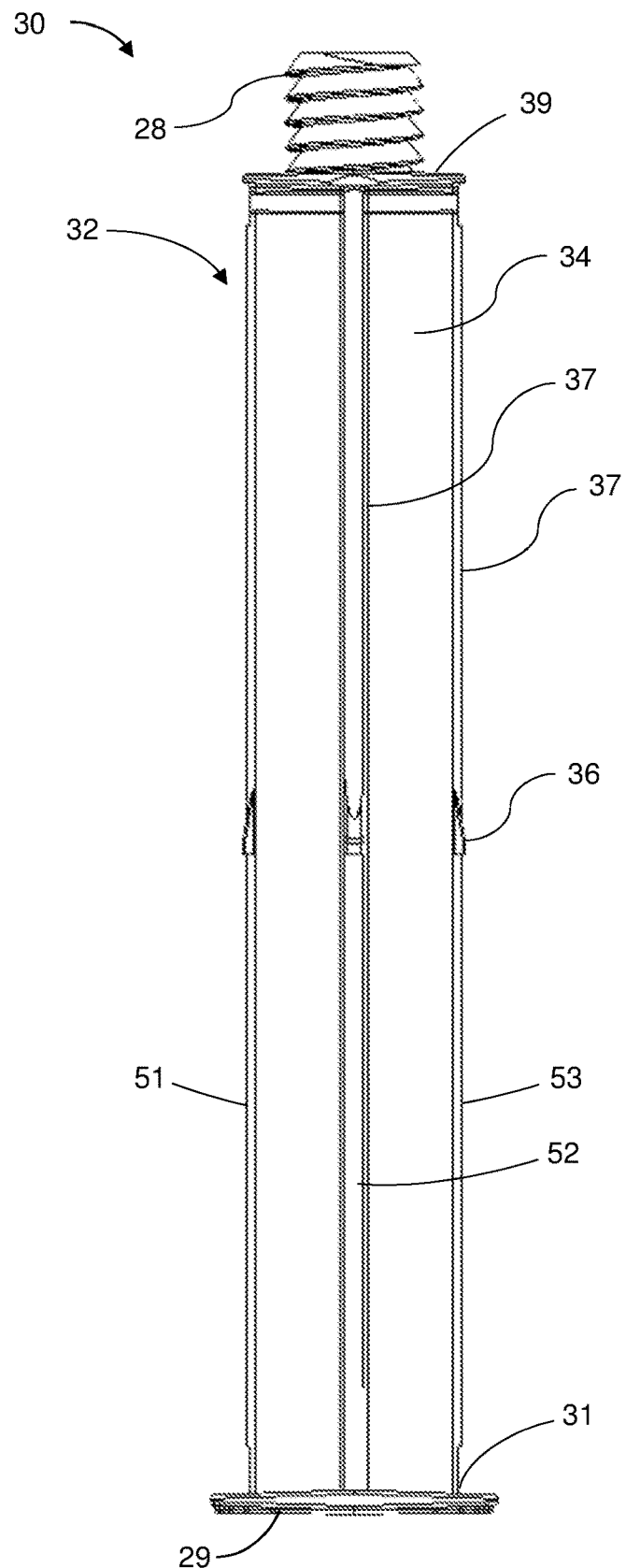
FIG. 3 illustrates a side view of a plunger rod according to one or more embodiments of the present disclosure.

As shown in FIGS. 1 and 3, a plunger rod 30 is provided and includes a plunger rod body 32 having a proximal end 31, and a distal end 39. The plunger rod 30 is slidably within the chamber 16 of the barrel 10 for driving fluid out of the chamber 16. The plunger rod body 32 of the plunger rod extends outwardly from the open proximal end 11 of the barrel and may be disposed within the chamber 16. The plunger rod 30 includes a thumb press 29 at the proximal end 31 and a stopper 40 at the distal end 39. The stopper 40 includes a sealing edge 42 that forms a seal with the inside surface 14 of the barrel. The shape of the plunger rod may be modified to fit within barrels with side walls having different shapes.

The plunger rod body 32 of the plunger rod includes an outside surface 34, forming a perimeter around the plunger rod body 32 and an axial length extending from the proximal end 31 to the distal end 39. The plunger rod body 32 may include a single beam or structure, which may have cylindrical or other shapes. As shown in FIGS. 1-9, the body portion 32 may be formed by two perpendicularly intersecting beams 37. The beams may have a rectangular cross-section. In the embodiment shown, the two intersecting beams 37 intersect to form an outside surface outlining four quadrants 51, 52, 53, 54 (shown more clearly in FIG. 3) that face the inside surface 14 of the barrel and extend along the axial length from the proximal end 31 to the distal end 39 of the plunger rod.

In a preferred embodiment, as illustrated in FIG. 3, the plunger rod body includes two intersecting beams 37 that intersect to form a perpendicular crossbar 44 having an outside surface outlining four quadrants of a cruciform. For purposes of illustration, three quadrants 51, 52, 53 of the four quadrants are shown. The perpendicular crossbars 44 are longitudinally integrated with the thumb press 29 and the stopper-engaging portion 28. The body of the rod plunger is not limited to being cruciform, nor do the crossbars 44 necessarily need to be perpendicular or symmetrical. The body of the rod plunger 32 may comprise of another geometric shape that can be inscribed within the chamber 16 of the syringe barrel 10. For instance, the body of the rod plunger may be triangular or rectangular.

A stopper-engaging portion 28 having a threaded region is disposed adjacent to the distal end 39 for fastening of a stopper. In one or more embodiments, the threaded region of the stopper-engaging portion 28 is configured to receive corresponding threads of a stopper. In a specific embodiment, the plunger rod and stopper may be integrally formed or permanently attached. In accordance with one or more embodiments of the present disclosure, the stopper-engaging portion 28 is shaped to fit within the stopper cavity of the stopper and to retain the stopper at the distal end of the plunger rod.

Adjacent to the threaded region is the plunger rod body. The plunger rod body is disposed within the chamber 16 and moveable in the proximal and distal direction within the chamber 16, respective to the syringe barrel 10.

The plunger rod body and the retaining element may be made of a rigid plastic or other material. Examples of such materials include polypropylene, polyethylene, polycarbonate and combinations thereof.

The stopper 40 of one or more embodiments may be integrally formed on the distal end 39 of the plunger rod or may form a separate component that is connected to the distal end 39 of the plunger rod. The distal end 39 of the plunger rod may include an integrally formed stopper. As shown in FIG. 1, the stopper 40 may include a conically-shaped distal surface and the barrel may include a conically-shaped inside surface at its distal wall. The stopper 40 is slidably positioned in fluid-tight engagement with the inside surface 14 of the barrel for drawing fluid into and driving fluid out of the chamber.

The stopper 40 may be made of any material suitable for providing a seal with the inside surface 14 of the barrel. For example, the stopper 40 may be made of thermoplastic elastomers, natural rubber, synthetic rubber or thermoplastic materials and combinations thereof. The stopper 40 may be integrally formed or composed of separate components of the same or different materials joined together. The plunger rod 30 may be made of material which is more rigid than the stopper such as polypropylene, polyethylene and the like. Materials should be chosen to be compatible with the procedure being used.

In the embodiments shown in FIGS. 1-9, one or more retention elements 36 are disposed on the outside surface of the body portion 32 of the plunger rod. More specifically, the one or more retention elements are disposed on the outside surface of the four quadrants (51, 52, 53). The retention elements 36 may be integrally formed or provided as separate components that may be added to the plunger rod. In one or more embodiments where retention elements 36 are provided as separate components, the plunger rod 30 or barrel 10 may further include a structure for the attachment of separate retention elements 36. In one or more embodiments, the chamber of the barrel may accommodate 10 mL of fluid. In one or more embodiments, the pre-filled fluid is a solution containing saline, heparin or citrate or other drugs or medicament. In one or more embodiments, the pre-filled fluid is a flush solution or a medicament. A 10 mL chamber 16 of the barrel may be prefilled with a predetermined amount of solution in a range from 0 mL to 10 mL, preferably 1 mL, 2 mL, 3 mL, 4 mL, 5 mL, 6 mL, 7 mL, 8 mL, 9 ml, and 10 mL, wherein the retention element disposed on the plunger rod of the present disclosure interacts with the retaining ring on the inside surface of the barrel to prevent the pre-filled solution from entering a non-sterile area of the syringe if the plunger rod is accidently pulled back by the end user. In one or more embodiments, the chamber 16 of the barrel is prefilled with 3 mL of solution. In one or more alternate embodiment, the chamber 16 of the barrel is prefilled with 5 mL of solution. In one or more embodiments, the retaining ring is disposed on the inside surface of the barrel at the proximal end of the barrel. In one or more embodiments, the retaining ring is disposed on the inside surface of the barrel to interact with the retention element of the plunger rod to allow a predetermined amount of fluid in a range from 0 mL to 10 mL, such as 3 or 5 mL, which was pre-filled in the chamber of the barrel and to prevent the pre-filled solution from entering a non-sterile area of the syringe if the plunger rod is accidently pulled back by the end user.

As shown in FIG. 1, one embodiment of the present disclosure relates to a syringe assembly 6 having a barrel whose chamber can be pre-filled with a predetermined amount of fluid in a range from 0 mL to 10 mL, such as 3 or 5 mL, and having retaining element 36 disposed at a fixed position along the length of a plunger rod body 32 to prevent the pre-filled solution from leaving a sterile area "A" and entering a non-sterile area "B" located beyond the retaining element 36 if the plunger rod is accidently pulled back by the end user into a non-sterile area.

In one or more embodiments, the plunger rod 30 includes an integral retaining element 36 along the length of a plunger rod body 32 to control the maximum relative position the plunger rod 30 can distally extend from the distal end 19 of the syringe assembly. When the retaining element 36 abuts against a retaining ring within the chamber 16 of the syringe barrel 10, the retaining element 36 of the plunger rod prevents the plunger rod from further extending from the distal end 19 of the syringe 6 beyond a desired point to prevent the pre-filled solution from entering a non-sterile area of the syringe when the plunger rod is accidently pulled back for partially pre-filled syringes. The position of the retaining element 36 on the plunger rod body 32 is determined by the amount of fluid volume that is prefilled into the syringe barrel 10 such that the retaining element 36 preventing the pre-filled solution from entering a non-sterile area of the syringe if the plunger rod is accidently pulled back by the end user.

In the present disclosure, a convention is followed wherein the medial direction is the direction pointing perpendicularly towards the longitudinal axis 5, and the lateral direction is the direction pointing perpendicularly away from the longitudinal axis 5.

Figure 2:
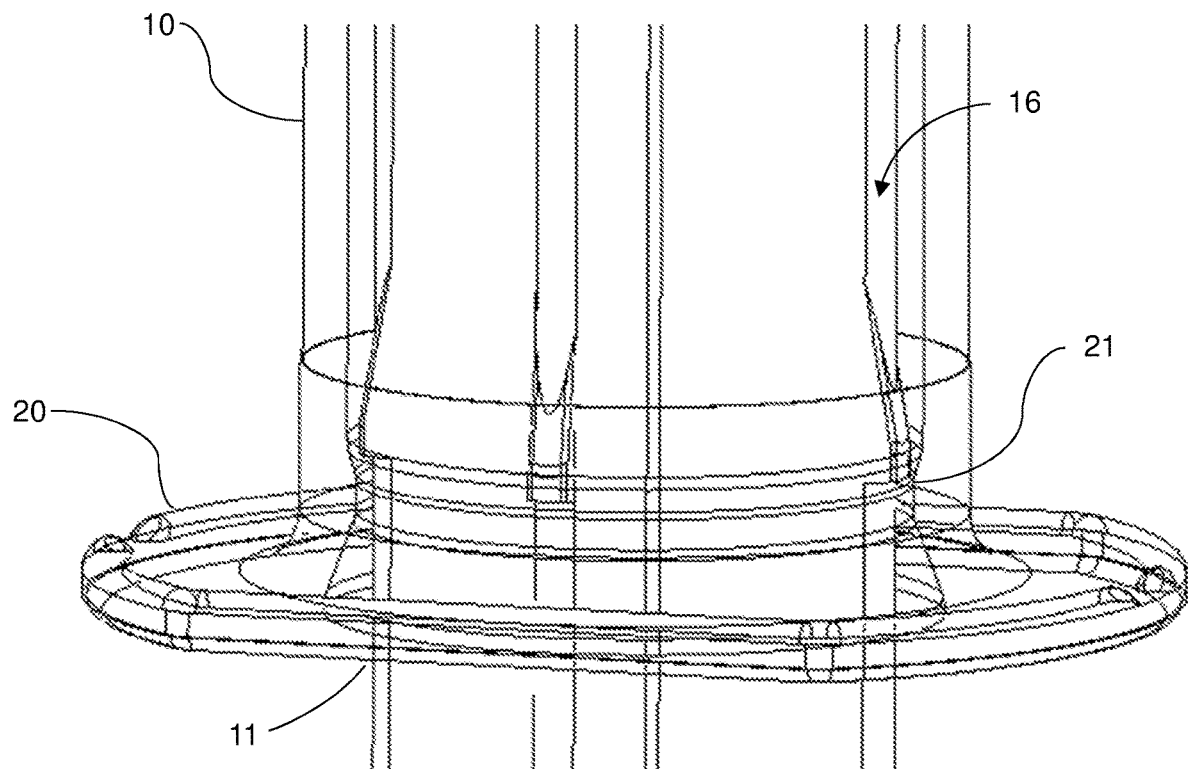
FIG. 2 shows a partial transparent top view of the interaction of a plunger rod and barrel of the syringe assembly shown in FIG. 1.

As shown in FIG. 2, the syringe barrel 10 comprises of a chamber 16. In one or more embodiments, the maximum volume of the chamber is 10 mL. In one or more embodiments of the present disclosure, the volume of prefilled fluid in chamber 16 can be in the range of 0 mL to 10 mL, preferably 1 mL, 2 mL, 3 mL, 4 mL, 5 mL, 6 mL, 7 mL, 8 mL, 9 ml, and 10 mL. Within the chamber 16 exists a retaining ring or retaining ring 21 closely adjacent proximal end 11 of the syringe barrel 10. Retaining ring 21 extends medially into the chamber 16 of the syringe barrel 10. The retaining ring 21 prevents the retaining element 36 from proximal translation once the retaining element 36 is approaching or abutted to the retaining ring 21 to prevent the pre-filled solution from entering a non-sterile area of the syringe when the plunger rod is accidently pulled back.

As shown in FIGS. 2 and 3, an alternate embodiment of the plunger rod 30 comprises one or more retention elements 36 disposed along the length of the crossbars 44 such that when the plunger rod is disposed into a 10 mL syringe barrel, the plunger rod will limit the pre-filled volume in the syringe chamber 16 in a range from 0 mL to 10 mL, e.g. 3 mL or 5 mL, and prevent the pre-filled solution from entering a non-sterile area of the syringe if the plunger rod is accidently pulled back by the end user. More specifically, the one or more retention elements are disposed on the outside surface of the four quadrants (51, 52, 53). The retaining element is disposed along the plunger rod body at the farthest medial end of the crossbars 44. The one or more retaining element is disposed along the plunger rod body at a length of a plunger rod body 32 to allow a user to administer a desired amount of flush solution or medicament in a range from 0 mL to 10 mL, e.g. 3 mL or 5 mL, depending on the location that the retaining element is disposed along the plunger rod. In one or more embodiments, the retaining element of the plunger rod interacts with a retaining ring or retaining ring 21 disposed on the inside surface of the chamber 16 of the syringe barrel 10 and extending radially inwardly toward the chamber and/or a plunger rod. The retaining ring 21 interacts with the retention elements 36 disposed on the plunger rod 30 to prevent the pre-filled solution from entering a non-sterile area of the syringe if the plunger rod is accidently pulled back by the end user. In such embodiments, the retaining ring 21 forms a narrowed cross-sectional width in comparison to the cross-sectional width formed by the inside surface 14 of the barrel. The inside surface 14 of the barrel has a smaller cross-sectional width at the retaining ring 21.

Figure 4:
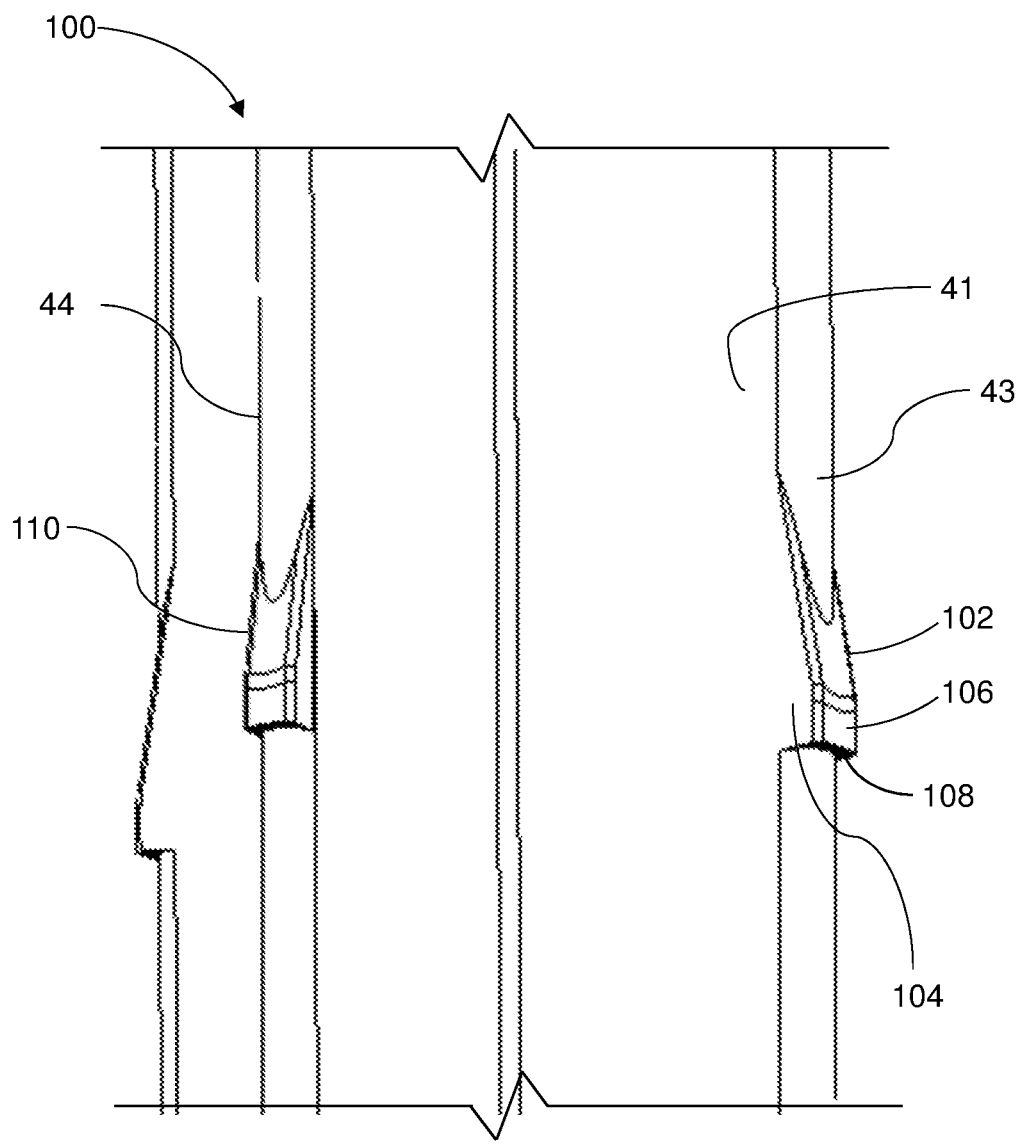
FIG. 4 illustrates a partial bottom-perspective view of the embodiment of the plunger rod shown in FIG. 3.

For one or more specific embodiment, as shown in FIG. 4, the mechanical stop of the plunger rod is disposed on crossbars 44 and include more than one straight walls 41 and a curved wall 43.

As shown in FIG. 4, the retaining element 100 is in the shape of a "shark fin". The retaining element 100 is a discontinuity along the length of the plunger rod body 32 on the curved wall 43. The retaining element 100 comprises of a sloped surface 102. The sloped surface 102 is outwardly tapered towards the proximal end 31 of the plunger rod body 32. The side walls 104 of the retaining element 100 are level with the straight wall 41 of the crossbar 44. The retaining element 100 may also have one or more flat portions 106 that run parallel to the longitudinal axis 5. There is a drop-off or ledge in the sloped surface that forms a flat end 108 of retaining element 100. The flat end 108 is perpendicular to the longitudinal axis 5.

In one or more embodiments, the retaining element 100 in the form of the "shark fin" protrudes radially from the outside surface of the four quadrants (51, 52, 53). In one or more embodiments, the retaining element 100 in the form of the "shark fin" has a thickness equal to or slightly less than a thickness of the four quadrants (51, 52, 53). In one or more embodiments, the retaining element 100 in the form of the "shark fin" does not project tangentially from the four quadrants (51, 52, 53).

Figure 5:
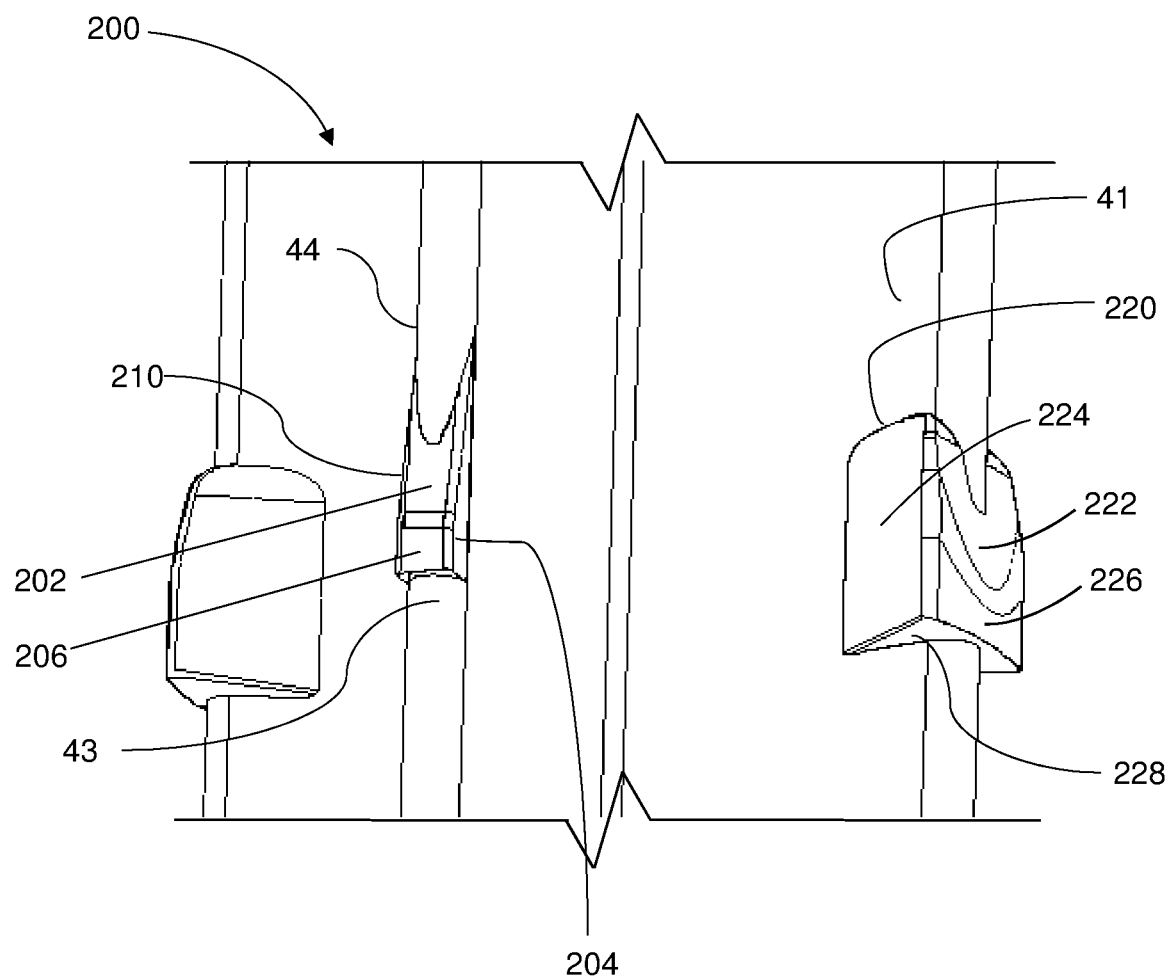
FIG. 5 illustrates a partial bottom-perspective view of an alternative embodiment of the plunger rod shown in FIG. 3.
Figure 6:
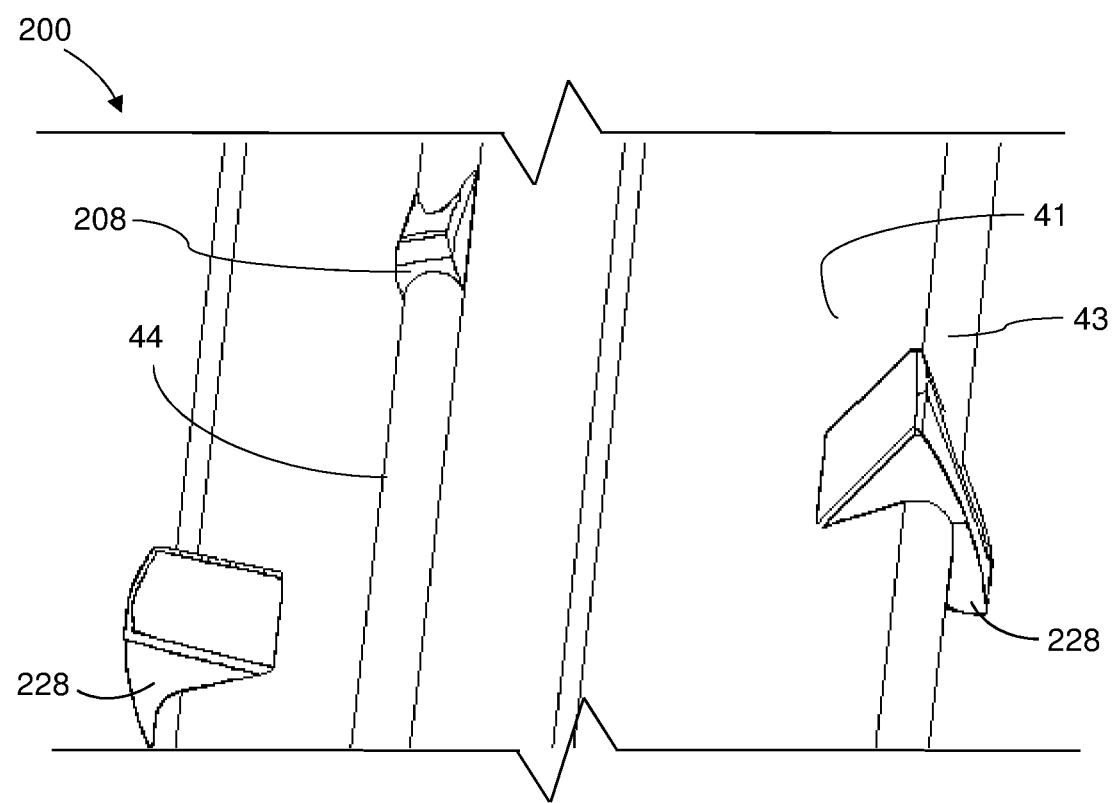
FIG. 6 illustrates a partial bottom-perspective view of an alternative embodiment of the plunger rod shown in FIG. 3.

As shown in FIGS. 5 and 6, an alternate embodiment of the plunger rod includes a retaining element 200 having two components disposed and integrated into wall 43 of alternating crossbars 44. The retaining element 200 is a discontinuity along the length of the plunger rod body 32 disposed on the curved wall 43. The first component 210 of the retaining element is in the shape of a "shark fin" and is integrated into the curved wall 43 of the crossbar 44 and comprises a sloped surface 202. The sloped surface 202 outwardly tapers towards the proximal end 31 of the plunger rod body 32. The side walls 204 of the retaining element 200 are level with the straight wall 41 of the crossbar 44. The retaining element 200 may also have one or more flat portions 206 that run parallel to the longitudinal axis 5. There is a drop-off or ledge in the sloped surface that forms a flat end 208 of retaining element 200. The flat end 108 is perpendicular to the longitudinal axis 5.

The second component 220 of the retaining element 200 is a discontinuity integrated into the curved wall 43 of alternating crossbars 44, wherein two of the crossbars 44 have the first component 210 in the form of the "shark fin" and alternating two of the crossbars have the second component 220. The second component 220 is in the shape of a tapered wedge and is integrated into the curved wall 43 of the crossbar 44. The second component 220 comprises of a sloped surface 222 that outwardly tapers towards the proximal end 31 of the plunger rod body 32. The retaining element 200 may also have one or more flat portions 226 that run parallel to the longitudinal axis 5. The side walls 224 of the second component 220 protrude outward from the midplane and extend medially onto the straight wall 41 of the crossbar 44 to "envelope" the crossbar 44 of the plunger rod body 32. Alike the sloped surface 222, the side walls 224 of the second component 220 outwardly tapers towards the proximal end 31 of the plunger rod body 32. There is a drop-off from the sloped surface 222 and the side walls 224 that form the flat end 228 of the second component 220 of the retaining element 200.

Within the body of the rod plunger, there may be only a single embodiment or a combination of embodiments of the retaining elements 100 and 200 used throughout the plunger rod body 32.

Figure 7:
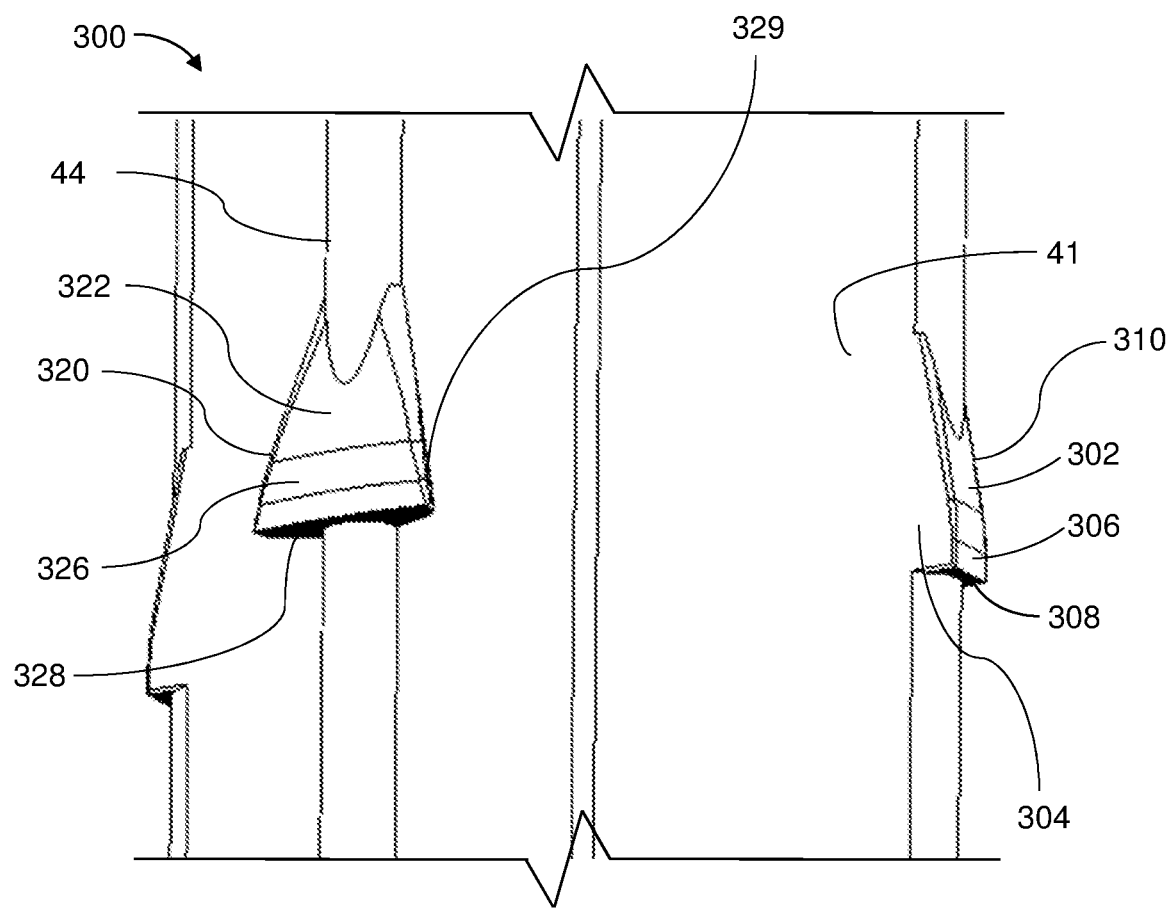
FIG. 7 illustrates a partial bottom-perspective view of an alternative embodiment of the plunger rod shown in FIG. 3.

As shown in FIG. 7, an alternate embodiment of the plunger rod includes a retaining element 300 having two components disposed and integrated into alternating crossbars. The retaining element 300 is a discontinuity along the length of the plunger rod body 32 on the curved wall 43. The first component 310 of the retaining element is in the shape of a "shark fin" and is integrated into the curved wall 43 of the crossbar 44 and comprises a sloped surface 302. The sloped surface 302 outwardly tapers towards the proximal end 31 of the plunger rod body 32. The side walls 304 of the first component 310 are level with the straight wall 41 of the crossbar 44. The first component 310 may also have one or more flat portions 306 that run parallel to the longitudinal axis 5. There is a drop-off or ledge in the sloped surface that forms a flat end 308 of the first component 310. The flat end 108 is perpendicular to the longitudinal axis 5.

The second component 320 of the retaining element is in the shape of a "shark tail" and is integrated into the curved wall 43 of alternating crossbars 44. The second component 320 comprises of a sloped surface 322. The sloped surface 322 outwardly tapers towards the proximal end 31 of the plunger rod body 32. The side wall 329 of the second component 320 protrudes outwards from the crossbar 44 and outwardly tapers towards the proximal end 31 of the plunger rod body 32, aligned with the sloped surface 322. The retaining element 300 may also have one or more flat portions 306 that run parallel to the longitudinal axis 5. There is a drop-off in the sloped surface 322 and the side wall 329 that forms a flat end 328 of the second component 320. The flat end 328 is perpendicular to the longitudinal axis 5.

Figure 8:
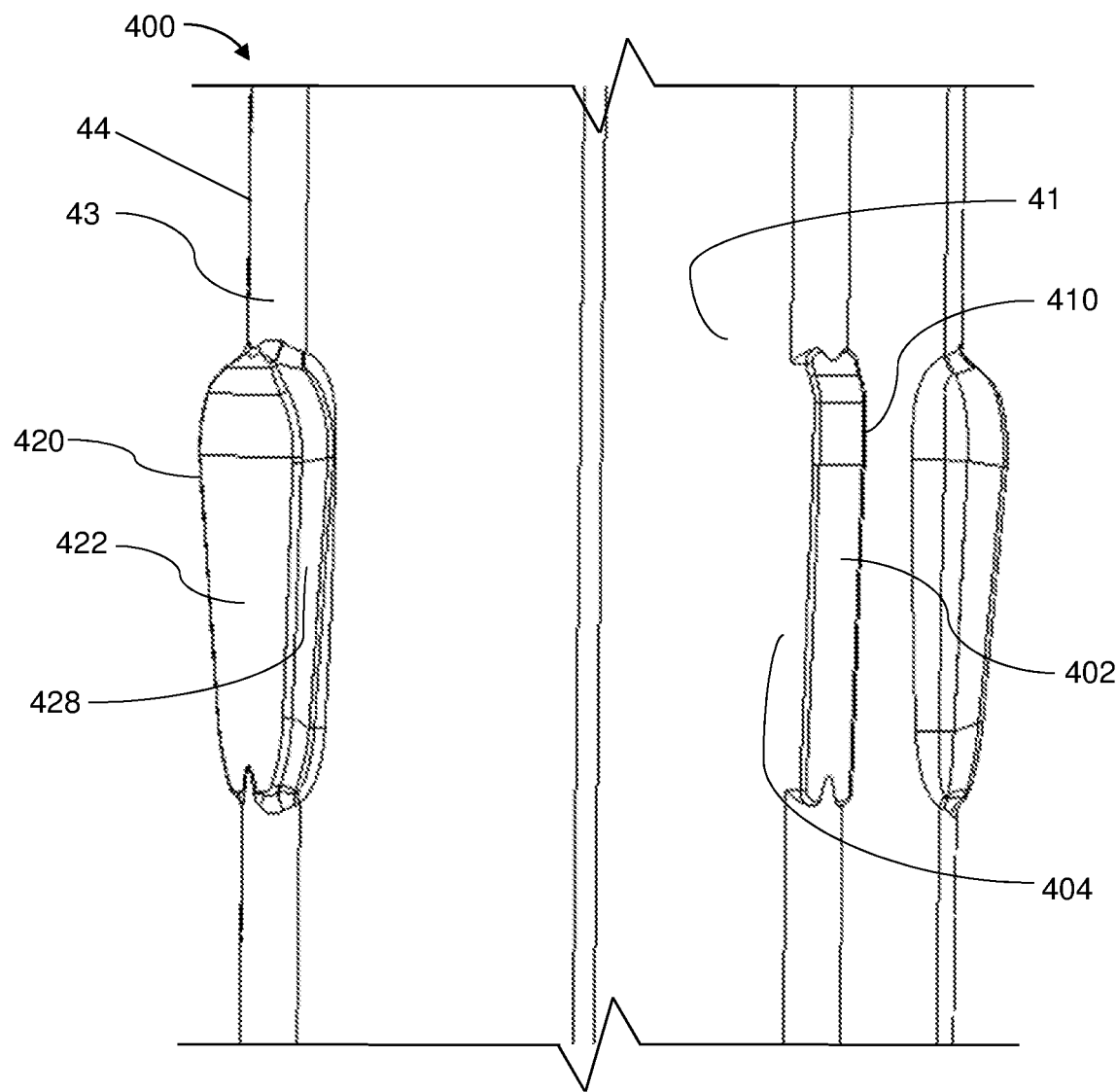
FIG. 8 illustrates a partial top-perspective view of an alternative embodiment of the plunger rod shown in FIG. 3.

As shown in FIG. 8, an alternate embodiment of the plunger rod includes a retaining element 400 having two components disposed and integrated into alternating crossbars. The retaining element 400 is a discontinuity along the length of the plunger rod body 32 on the curved wall 43. The first component 410 of the retaining element is in the shape of a "tear drop" and is integrated into the curved wall 43 of the crossbar 44 and comprises a sloped surface 402. The sloped surface 402 outwardly tapers towards the distal end 39 of the plunger rod body 32. The opposite tapering design provides a resistive force to the sloped surface 402 as it frictionally engages with the retaining ring 21 and prevents the pre-filled solution from entering a non-sterile area of the syringe when the plunger rod is pulled back. This results in a stoppage of the proximal translation of the plunger rod 30 relative to the syringe barrel 10. The side walls 404 of the retaining element 400 are level with the straight wall 41 of the crossbar 44.

In one or more embodiments, the first component 410 protrudes radially from the outside surface of the four quadrants (51, 52, 53). In one or more embodiments, the first element 410 has a thickness equal to or slightly less than a thickness of the four quadrants (51, 52, 53). In one or more embodiments, the first element 410 in the form does not project tangentially from the four quadrants (51, 52, 53).

The second component 420 of the retaining element 400 is in the shape of a "submarine" and is integrated into the curved wall 43 of alternating crossbars 44 and comprises a sloped surface 422. The sloped surface 422 of the second component 420 outwardly tapers towards the distal end 39 of the plunger rod body. The sloped surface 402 outwardly tapers towards the distal end 39 of the plunger rod body 32. The sloped surface 422 of the second component 420 outwardly tapers providing a resistive force to the sloped surface 422 as it frictionally engages with the retaining ring 21 when the plunger rod is accidently pulled back by an end user. This causes a stoppage of the proximal translation of the plunger rod 30 relative to the syringe barrel 10. The second component 420 also comprises of a side wall 428 that medially extends into the crossbar 44. In one or more embodiments the second component 220 protrudes tangentially with respect to the curved wall 43. In one or more embodiments, the second component 220 also contacts and envelopes a portion of the crossbars 44 of which they are situated upon.

In one or more embodiments, the first component 410 of the retaining element and the second component 420 of the retaining element are disposed on alternating crossbars 44, wherein two of the crossbars 44 have first component 410 and alternating two of the crossbars have the second component 420.

In one or more embodiments, the plunger rod 30 may comprise a combination of the retaining element with or without walls that are level to the straight wall of the crossbar.

One or more embodiments of the plunger rod having retaining element 400 provides the end user with a prolonged period of time to stop the pull back motion as the resistance force builds up.

Figure 9:
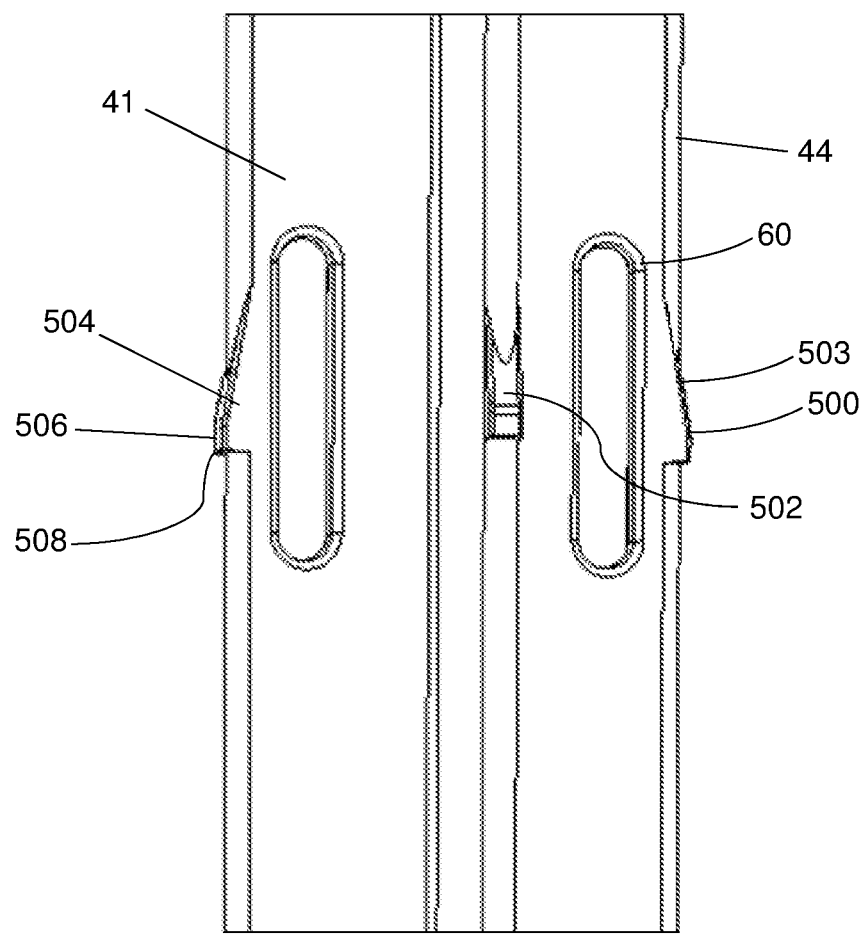
FIG. 9 illustrates a partial perspective view of an alternative embodiment of the plunger rod shown in FIG. 3.

An alternate embodiment of the plunger rod is shown in FIG. 9. As shown in FIG. 9, the retaining element 500 is in the shape of a "shark fin". The retaining element 500 is a discontinuity along the length of the rod plunger body 32 on the curved wall 43. The retaining element 500 comprises of a sloped surface 502. The sloped surface 502 outwardly tapers towards the proximal end 31 of the plunger rod body 32. The side walls 504 of the retaining element 500 are level with the straight wall 41 of the crossbar 44. The retaining element 500 may also have one or more flat portions 506 that run parallel to the longitudinal axis 5. There is a drop-off or ledge in the sloped surface that forms a flat end 108 of retaining element 100. The flat end 508 is perpendicular to the longitudinal axis 5. In one or more embodiments, the retaining element 500 further comprises a plurality of tangential ribs 503 disposed upon the sloped surface 502

Medial to the retaining element 500 on the plurality of crossbars 44 exists a slotted hole 60 along the plunger rod 30 as shown in FIG. 9. The slotted holes allow the retaining element 500 to deflect in a medial and lateral direction. The slotted hole 60 allows flexure of the retaining element 500 and the surface it is integrated on. This added flexibility allows for the plunger rod 30 to be assembled within the syringe barrel 10. To assemble the medical syringe 6, the distal end of the plunger rod 30 is inserted into the proximal end 11 of the syringe barrel 10. As the plunger rod enters the syringe barrel, the retaining ring 21 within the chamber 16 of the syringe barrel 10 exerts a force on the sloped surface 502 of the retaining element 500. The slotted hole 60 on the straight wall 41 of the crossbars 44 allow for the retaining element 500 to deflect in the medial direction. Once the flat end 508 on the retaining element 500 clears the retaining ring 21 in the syringe barrel 10, the retaining element 500 snaps back from its deflected position and produces an audible "click" upon completion of the assembly of the medical syringe 6.

In one or more embodiments, a plunger rod having a combination of any of the retaining elements described herein may also include the slotted hole 60 in the plurality of crossbars 44.

As shown in FIGS. 1-9, a plurality of retaining element may be disposed along the axial length of the plunger rod and may be disposed at pre-defined intervals along the axial length. In a specific embodiment, the pre-defined intervals are equally spaced. The plurality of retaining elements may be disposed along the axial length of the plunger rod determined by the amount of pre-filled solution in a range from 0 mL to 10 mL, such as 3 mL or 5 mL, such that the stopper is prevented from being pulled back to the point where the pre-filled solution can enter the non-sterile area behind the original location of the back of the stopper rib.

In one or more embodiments, one or more retaining element 36 may be peripherally formed along a segment of the outside surface of the plunger rod, while the remaining segments of the outside surface are free of any retaining element.

The one or more retaining element 36 of plunger rod body 32 interact with the retaining ring 21 of the syringe barrel when a force is applied to the plunger rod in the proximal direction caused by accidental pull back by the end user.

In operation, the syringe assemblies when used with the plunger rods described herein are pre-filled with flush solution or medicament using known methods. The pre-filled syringe undergoes a terminal sterilization process via either autoclave or radiation sterilization in the manufacturing plant to produce sterile pathways of the pre-filled liquid. In one or more embodiments, the flush solution may be any solution intended for flushing or maintaining the performance of vascular access devices (VADs). Exemplary flush solutions include saline flush solution and/or heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml. Once assembled, the syringe assembly may be used by the end user to administer a pre-filled medicament or flushing a VAD such as a catheter of an I.V. set by providing a distal force. In order to protect from accidental pull-back, the retaining features described in the present disclosure prevent the stopper being pulled back to the point where the solution can enter the non-sterile area behind the original location of the back of the stopper rib.

In accordance with one or more embodiments, the one or more retaining element 36 disposed on the plunger rod are shaped to interfere or form enhanced mechanical interference with the syringe barrel during movement of the plunger rod in the proximal direction. Changes in mechanical forces between the plunger rod and barrel impede, slow or stop movement of the plunger rod in the event that the user applies an accidental force to the plunger rod in the proximal direction.

Figure 10:
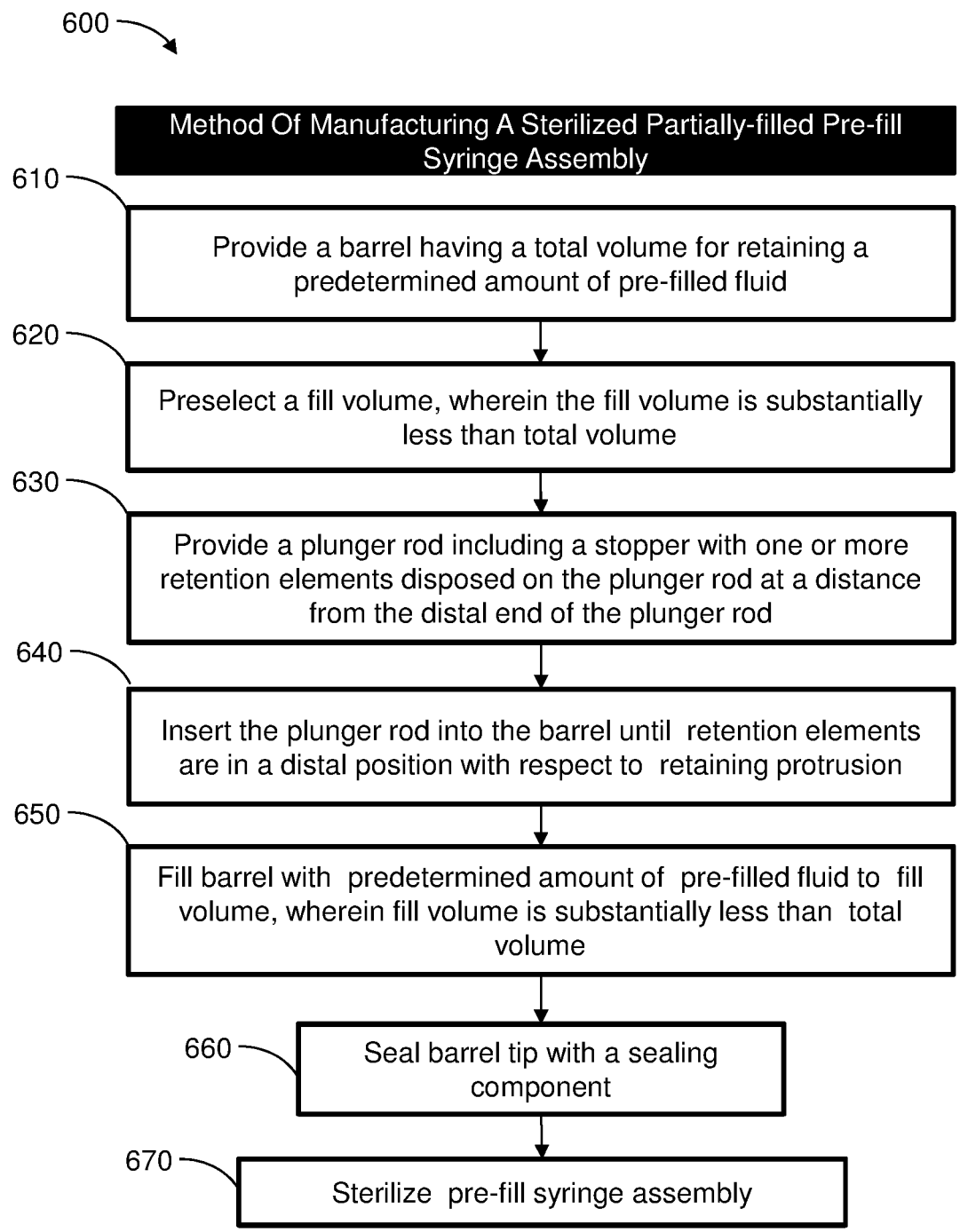
FIG. 10 is a flowchart illustrating a method of manufacturing a sterilized partially-filled pre-fill syringe assembly.

Another aspect of the present disclosure pertains to a method of manufacturing a sterilized partially-filled pre-fill syringe assembly. An exemplary method of manufacture 600 is shown in FIG. 10. The reference numerals used to describe the various elements below coincide the elements shown in FIGS. 1-9. As shown in step 610 of FIG. 10, a barrel 10, as shown in FIG. 1, is provided including a side wall 12 having an inside surface 14 defining a chamber 16 having a total volume for retaining a predetermined amount of pre-filled fluid, an open proximal end 11 having a retaining protrusion and a distal end 19 including a distal wall 17 with a tip extending distally therefrom having a passageway therethrough in fluid communication with said chamber. As shown in step 620 of FIG. 10, a fill volume is preselected, wherein said fill volume is substantially less than said total volume. As shown in step 630 of FIG. 10, a plunger rod 30 of one or more embodiments described in the present disclosure and as shown in FIGS. 1-9 is provided. The plunger rod 30 includes a distal end, a stopper and a proximal end. The plunger rod includes one or more retention elements, as described in the present disclosure, disposed on the plunger rod at a distance from the distal end of the plunger rod, said distance correlated to said fill volume. The one or more retention elements 36 are configured to provide increased mechanical interference between the plunger rod 30 and barrel 10 retaining protrusion. As shown in step 640 of FIG. 10, the plunger rod is inserted into the barrel 10 until said retention elements are in a distal position with respect to the retaining protrusion. As shown in step 650 of FIG. 10, the barrel 10 is filled with the predetermined amount of the pre-filled fluid to said fill volume, wherein said fill volume is substantially less than said total volume. As shown in step 660 of FIG. 10, the barrel tip is sealed with a sealing component. In one or more embodiments, the sealing element is a tip cap. As shown in step 670 of FIG. 10, the pre-fill syringe assembly is sterilized. In one or more embodiment, the pre-filled syringe undergoes a terminal sterilization process via either autoclave or radiation sterilization in the manufacturing plant to produce sterile pathways of the pre-filled liquid. In one or more embodiments, the step of sterilizing said pre-fill syringe assembly occurs before inserting the plunger rod into the barrel until said retention elements are in a distal position with respect to said retaining protrusion.

In one or more embodiments, the total volume is approximately 3.33 times the fill volume. In a specific embodiment, the total volume is approximately 10 ml and the fill volume is 3 ml.

In one or more alternate embodiment, the total volume is approximately 2 times the fill volume. In a specific embodiment, the total volume is approximately 10 ml and the fill volume is 5 ml.

In one or more embodiments, the one or more retention elements includes a first component having two side walls being level with a straight wall of a crossbar, a sloped top surface having a grade in a range from 1%-100%, one or more flat portions oriented parallel to a longitudinal axis, and a ledge in the sloped top surface that forms a flat end of oriented perpendicular to the longitudinal axis, as shown in FIGS. 3 and 4.

In one or more alternate embodiment, the one or more retention elements further includes a second component having a tapered wedge that radially protrudes from the straight wall with respect to a medial edge, as shown in FIG. 5-7.

In yet another alternate embodiment, the one or more retention elements further includes a second component having an oblong protrusion that tapers from the distal end to the proximal end and extends from a curved wall of the crossbar, as shown in FIG. 8.

In yet another alternate embodiment, the one or more retention elements further includes a second component having a slotted hole in the sidewall of the crossbar positionally aligned behind the retention element along the plunger rod, as shown in FIG. 9.

In one or more alternate embodiment, the retaining protrusion is a disk, gasket or O-ring.

Reference throughout this specification to "one embodiment," "certain embodiments," "one or more embodiments" or "an embodiment" means that a particular element, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular elements, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe assembly comprising:
a barrel including a side wall having an inside surface defining a chamber for retaining a predetermined amount of pre-filled fluid,
an open proximal end and a distal end including a distal wall with a tip extending distally therefrom having a passageway therethrough in fluid communication with said chamber;
a plunger rod disposed within the barrel, the plunger rod comprising a distal end, a proximal end and an outside surface, wherein the distal end of the plunger rod including a stopper having a distal face, a plunger rod body extending from the proximal end of the plunger rod to the distal end of the plunger rod; and
one or more retention elements disposed on the plunger rod at a length from the distal end of the plunger rod configured to provide increased mechanical interference between the plunger rod and barrel when a force is applied in a proximal direction to prevent the pre-filled fluid from entering a non-sterile area of the syringe assembly, wherein the one or more retention elements comprise a first component having two side walls being level with a straight wall of a crossbar, a sloped top surface having a grade in a range from 1%-100%, one or more flat portions oriented parallel to a longitudinal axis, and a ledge in the sloped top surface that forms a flat end of oriented perpendicular to the longitudinal axis.

2. The syringe assembly of claim 1, wherein the one or more retention elements comprises a plurality of discontinuities disposed on the outside surface of the plunger rod.

3. The syringe assembly of claim 2, wherein the one or more retention elements extend radially outwardly toward the inside surface of the barrel.

4. The syringe assembly of claim 1, wherein the predetermined amount of pre-filled fluid is in a range from 0 mL to 10 mL.

5. The syringe assembly of claim 4, wherein the predetermined amount of pre-filled fluid is 3 mL.

6. The syringe assembly of claim 4, wherein the predetermined amount of pre-filled fluid is 5 mL.

7. The syringe assembly of claim 1, wherein the one or more retention elements comprise:
at least one discontinuity disposed on the outside surface of the plunger rod, the discontinuity extending radially outwardly toward the inside surface of the barrel; and
at least one retaining ring disposed on the inside surface of the barrel, the retaining ring extending radially inwardly toward the outside surface of the plunger rod, the at least one discontinuity cooperating with the at least one retaining ring to increase an interference between the plunger rod and the barrel to require an increased mechanical force to stop the plunger rod from advancing in a proximal direction.

8. The syringe assembly of claim 7, wherein movement of the plunger rod in a proximal direction creates an interference between a retaining ring disposed on an inside surface of the barrel and the one or more retention elements of the plunger.

9. The syringe assembly of claim 1, wherein a portion of the outside surface of the plunger rod is free of retention elements.

10. The syringe assembly of claim 1, wherein the one or more retention elements further comprise a second component having a tapered wedge that radially protrudes from the straight wall with respect to a medial edge.

11. The syringe assembly of claim 1, wherein the one or more retention elements further comprises a second component having an oblong protrusion that tapers from the distal end to the proximal end and extends from a curved wall of the crossbar.

12. The syringe assembly of claim 1, wherein the one or more retention elements further comprises a second component having a slotted hole in a sidewall of the crossbar positionally aligned behind the retention element along the plunger rod.

13. The syringe assembly of claim 1, wherein the pre-filled fluid is a solution containing saline, heparin or citrate or other drugs.

14. The syringe assembly of claim 1, wherein the fluid is a pre-filled medicament.

15. The syringe assembly of claim 1, wherein the syringe assembly is terminally sterilized.

16. A method of manufacturing a sterilized partially-filled pre-fill syringe assembly comprising:
providing a syringe assembly of claim 1;
preselecting a fill volume, wherein said fill volume is substantially less than said total volume;
inserting the plunger rod into the barrel until said retention elements are in a distal position with respect to a retaining protrusion;
filling said barrel with a predetermined amount of said pre-filled fluid to said fill volume, wherein said fill volume is substantially less than a total volume;
sealing a barrel tip with a sealing component; and
sterilizing said pre-fill syringe assembly.

17. The method of claim 16, wherein the total volume is approximately 3.33 times the fill volume.

18. The method of claim 17, wherein the total volume is approximately 10 ml and the fill volume is 3 ml.

19. The method of claim 16, wherein the total volume is approximately 2 times the fill volume.

20. The method of claim 19, wherein the total volume is approximately 10 ml and the fill volume is 5 ml.

21. The method of claim 16, wherein the retaining protrusion is a disk, gasket or O-ring.

22. The method of claim 16, wherein the sterilizing said pre-fill syringe assembly occurs before inserting the plunger rod into the barrel until said retention elements are in a distal position with respect to said retaining protrusion.

* * * * *